(12) United States Patent
Schuster et al.

(10) Patent No.: US 10,856,950 B2
(45) Date of Patent: Dec. 8, 2020

(54) MEDICAL STERILIZATION CONTAINER

(71) Applicant: Aesculap AG, Tuttlingen (DE)

(72) Inventors: Stefan Schuster, Grafenhausen (DE);
Matthias Henke, Fridingen (DE);
Selina Kammerer, Dauchingen (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 16/336,298

(22) PCT Filed: Sep. 22, 2017

(86) PCT No.: PCT/EP2017/074031
§ 371 (c)(1),
(2) Date: Mar. 25, 2019

(87) PCT Pub. No.: WO2018/055086
PCT Pub. Date: Mar. 29, 2018

(65) Prior Publication Data
US 2019/0298472 A1 Oct. 3, 2019

(30) Foreign Application Priority Data

Sep. 26, 2016 (DE) ........................ 10 2016 118 083

(51) Int. Cl.
*A61B 50/30* (2016.01)
*A61L 2/07* (2006.01)
(Continued)

(52) U.S. Cl.
CPC ................ *A61B 50/30* (2016.02); *A61L 2/07* (2013.01); *A61L 2/26* (2013.01);
(Continued)

(58) Field of Classification Search
CPC .......... A61L 2/07; A61L 2/26; A61L 2202/24; A61B 50/30; A61B 50/311; A61B 50/33;
(Continued)

(56) References Cited

U.S. PATENT DOCUMENTS 5,372,787 A 12/1994 Ritter
9,226,986 B2 1/2016 Gray-Dreizler et al.
(Continued)

FOREIGN PATENT DOCUMENTS

CN 201048988 Y 4/2008
CN 103480022 A 1/2014
(Continued)

OTHER PUBLICATIONS

International Search Report and Written Opinion for International Application No. PCT/EP2017/074031, dated May 3, 2018, 10 pages.
(Continued)

*Primary Examiner* — Lessanework Seifu

(57) ABSTRACT

A medical sterilization container has a tub-like first container part, a cover-like second container part, a filter device which is disposed or mounted, particularly from outside, on at least one of the container parts, and a sterilization container closure, which includes at least one closing flap that can be disposed on one of the container parts between a closed position and an open position for the purpose of closing the two container parts one to the other. When in the closed position, the closing flap locks and/or fastens and/or secures the filter device to the container part on which the filter device is disposed or mounted.

15 Claims, 2 Drawing Sheets

(51) Int. Cl.
  *A61L 2/26* (2006.01)
  *A61B 50/00* (2016.01)
(52) U.S. Cl.
  CPC ... *A61B 2050/005* (2016.02); *A61B 2050/007* (2016.02); *A61B 2050/0067* (2016.02)
(58) Field of Classification Search
  CPC .............. A61B 50/34; A61B 2050/005; A61B 2050/055; A61B 2050/007; A61B 2050/075; A61B 2050/0074
  See application file for complete search history.

(56) References Cited

U.S. PATENT DOCUMENTS

| | | |
|---|---|---|
| 9,388,080 B2 | 7/2016 | Weisshaupt et al. |
| 9,533,061 B2 | 1/2017 | Gray-Dreizler et al. |
| 9,888,977 B2 | 2/2018 | Thomas et al. |
| 2015/0225136 A1 | 8/2015 | Weisshaupt et al. |
| 2015/0374868 A1 | 12/2015 | Bruce et al. |
| 2016/0151123 A1 | 6/2016 | Thomas et al. |

FOREIGN PATENT DOCUMENTS

| | | |
|---|---|---|
| DE | 9212315 U1 | 11/1992 |
| DE | 10210889 A1 | 9/2003 |
| DE | 202005021090 U1 | 4/2007 |
| DE | 202009001010 U1 | 5/2009 |
| DE | 102012101833 A1 | 9/2013 |
| DE | 102012215121 A1 | 5/2014 |
| DE | 102013112129 A1 | 5/2015 |
| DE | 102014117517 A1 | 6/2016 |
| JP | 2001112857 A | 4/2001 |
| WO | 9207588 A1 | 5/1992 |
| WO | 2013131760 A1 | 9/2013 |

OTHER PUBLICATIONS

German Search Report for German Application No. 10 2016 118 083.1, dated Mar. 22, 2017 with translation, 13 pages.
Chinese Search Report received in Application No. 201780059094.1 dated Jun. 27, 2020, 8 pages.
First Chinese Office Action received in Application No. 201780059094.1 dated Jul. 2, 2020, 24 pages.
European Search Report received in Application No. 20151609.3 dated Sep. 17, 2020, 18 pages.

MEDICAL STERILIZATION CONTAINER

RELATED APPLICATIONS

This application is the United States national phase entry of International Application No. PCT/EP2017/074031, filed Sep. 22, 2017, which claims the benefit of priority of German Application No. DE 10 2016 118 083.1, filed Sep. 26, 2016. The contents of International Application No. PCT/EP2017/074031 and German Application No. DE 10 2016 118 083.1 are incorporated by reference herein in their entireties.

FIELD

The invention relates to a medical sterilization container comprising a tub-like first container part; a cover-like second container part; and a filter device which is disposed or mounted, particularly from outside, on at least one container part, in particular on a first lateral wall of the tub-like first container part. Furthermore, the invention relates to a method for sterilizing objects, in particular medical devices, in a sterilization container.

BACKGROUND

Sterile containers are generally known from the state of the art and are used in medicine in particular to sterilize or disinfect surgical instruments, implants and the like and to store or transport them for a short period after sterilization. Objects to be sterilized are generally first placed in the sterilization container or in a tub-like first container part of the sterilization container. Then, a cover-like second container part is arranged on the tub-like first container part and the two container parts are closed one to the other. The closed sterilization container is transported to a sterilizer. In this sterilizer, the objects to be sterilized inside the container are sterilized or disinfected in any sterilization process (e.g. hot air sterilization, steam sterilization, etc.).

It is known from the state of the art to equip sterilization containers with filter devices which prevent germs, bacteria or similar substances from entering the sterilization container and enable sterile media exchange during sterilization.

For example, sterilization containers are known in which the filter device can be mounted and dismounted from the sterilization container interior/from the inside. If the filter device is mounted from the inside, there is often the disadvantage that the filter device can only be checked for possible damage by a sterile user, in particular a nurse, after the sterilized objects, in particular the sterilized medical instruments, have been removed, especially if said filter device is mounted on a lateral wall. If it is then determined that the filter device is damaged, the removed objects must be sterilized again, a possibly contaminated instrument table on which the removed objects have been deposited in the meantime must be cleaned and the sterile user must change clothes if necessary. Thus, filter devices that can be mounted and dismounted from the inside are disadvantageous in many respects.

There are filter devices known from prior art which can be mounted and dismounted from the sterilization container outer side/from outside. However, the known solutions with externally mountable and dismountable filter devices have the disadvantage that the filter device can always be dismounted and remounted after sterilization without this being visible later on. A user can thus not see whether the filter device has already been opened or removed after sterilization and thus whether the sterilized objects in the sterilization container are still sterile when they are removed.

SUMMARY

Against this background, it is the object of the present invention to provide a sterilization container and a method for sterilizing objects which allow sterile media exchange, prevent the penetration of bacteria, germs or dust particles into the sterilization container and ensure sterile removal of sterilized objects. In particular, the disadvantages arising from the state of the art should be avoided or at least mitigated.

The invention primarily relates to a medical sterilization container comprising a tub-like first container part; a cover-like second container part; a filter device which is disposed or mounted, particularly from outside, on at least one container part, particularly on a first lateral wall of said tub-like first container part; and a sterilization container closure, which in particular can be sealed, which comprises at least one closing flap which can be disposed on one of the container parts between a closed position and an open position for the purpose of closing the two container parts one to the other, wherein, when in the closed position, said closing flap locks and/or fastens and/or secures the filter device to the container part on which said filter device is disposed or mounted, particularly to the first lateral wall of the tub-like first container part, in particular covers it at least in part.

The tub-like first container part consists basically of a bottom and lateral walls extending from the bottom, preferably vertically upwards. In particular, four lateral walls are provided. The cover-like second container part may be pivotally connected to the tub-like first container part or may be completely removable.

The filter device of the present invention can preferably be mounted/arranged/fixed/fastened from the outside to either the tub-like first container part or the cover-like second container part. According to the invention, the filter device can thus be mounted to the bottom or to one of the lateral walls of the tub-like first container part as well as to the cover-like second container part, i.e. the cover. However, in an advantageous embodiment of the present invention, the filter device is mounted/arranged on a first lateral wall which is any lateral wall of the preferably four lateral walls of the tub-like first container part.

The tub-like first container part and the cover-like second container part can be closed to one another via a sterilization container closure, which can be designed, for example, as a latching closure, a toggle-joint closure, a combination of latching closure and toggle-joint closure, etc. According to the invention, the sterilization container closure has at least one closing flap which can basically be brought into an open position and into a closed position. In the closed position of the closing flap, the two container parts are closed to one another. The closure can preferably be sealed in the closed position of the closing flap.

The filter device is secured to the sterilization container in its closed position by the closing flap. In other words, in the closed position of the closing flap, the filter device is at least partially covered by the closing flap. In this context, it is advantageous if the closing flap in the closed position covers the filter device in such a way that removal of the filter device is prevented. Hence, if the closing flap is in the closed position, it is impossible to remove the filter device from the sterilization container.

Thus, preferably in the open position of the sterilization container closure, in particular of the closing flap, the filter device is detachable from the container part on which the filter device is disposed or mounted, in particular from the first lateral wall of the tub-like first container part, and in the closed position of the sterilization container closure, in particular of the closing flap, is secured to the container part on which the filter device is disposed or mounted, in particular to the first lateral wall of the tub-like first container part, and is thus not detachable.

In accordance with the invention, the filter device can thus only be removed or detached from the sterilization container/from one of the two container parts, in particular from a first lateral wall of the tub-like first container part, if the sterilization container closure has previously been opened, i.e. if the closing flap has previously been moved from the closed position to the open position. This has the advantage that the filter device cannot be dismantled and reassembled undetected for a later user after sterilization. If the sterilization container is closed, especially if the sterilization container closure is sealed in the closed position of the closing flap, the user therefore knows that the filter device could not be opened or removed beforehand.

An advantageous exemplary embodiment is characterized in that the container part, on which the filter device is disposed or mounted, in particular the first lateral wall of the tub-like first container part, has a seating or recess, in particular in the form of a groove-shaped indentation, and a locking element/a locking portion, and the sterilization container closure comprises a latching element/a latching portion on the container part on which the filter device is disposed or mounted, in particular on the first lateral wall of the tub-like first container part, wherein the filter device, in the open position of the closing flap, can be inserted and/or mounted in the seating or recess from outside/from the sterilization, container outer side, and can be fixed and/or locked via the locking element to the container part, on which the filter device is disposed or mounted, and wherein the closing flap is engaged in the latching element/the latching portion in the closed position, thereby locking the two container parts to one another and covering the filter device at least in sections.

In other words, on the container part on which the filter device is mounted/arranged, in particular on the first lateral wall of the tub-like first container part, both a seating/recess/channel-shaped indentation and a latching element, in particular a latching projection, as well as a locking element, in particular a locking projection, are provided in an advantageous manner. The filter device is first inserted into the seating/recess/channel-shaped indentation so that an edge section of the filter device is received therein. The filter device can now already rest completely against the tub-like first or cover-like second container part. However, it is also conceivable that the filter device must be manually pressed and held against the corresponding container part by a user. Another, preferably opposite edge section of the filter device is now preferably in a position adjacent to the locking element and is locked/fixed to the corresponding container part via the locking element. If the closing flap engages in the latching element, the other, preferably opposite edge section of the filter device can even be pressed against the corresponding container part by the closing flap. This can be achieved in particular by the closing flap covering/overlapping the filter device at least in sections when in the engaged closed position. The core idea of the present invention is thus implemented in this preferred embodiment in a constructively simple manner.

It is also useful if the latching element, in particular the latching projection, in the closed position of the closing flap is received in a receiving recess provided on the closing flap, and a seal for sealing the sterilization container and for securing the sterilization container closure in the closed position of the closing flap can be passed through the latching element, in particular the latching projection.

In other words, in its closed position the closing flap engages in the latching element in such a way that the latching element is received in the receiving recess of the closing flap. The latching element is advantageously connected to the container part on which the filter device is mounted or arranged, and may even be an integral/one-piece/one-material section, in particular a latching section, of the container part. If the latching element has a projection, in particular a latching projection, which completely penetrates the closing flap, in particular the receiving recess of the closing flap in the closed position or projects outwards with respect to the closing flap in the closed position and this latching projection has a suitable recess, a seal can easily be attached to the latching element or the latching projection.

The sealed sterilization container is therefore always sealed and secured. Opening the sterilization container and concomitantly releasing or detaching the filter device from the tub-like first or cover-like second container part is therefore only possible by destroying the seal. If an undamaged seal is present on a sealed sterilization container, the user knows that the filter device could not be opened or removed beforehand.

It is also advantageous if the filter device comprises an externally provided filter holder and a filter element held/mounted/fastened on the filter holder, and the filter holder has a window for a user to check a state of the filter element from a sterilization container outer side.

A user can see through the window provided on the filter holder whether a filter element/filter is inserted or whether the inserted filter element is possibly damaged without having to open the sterilization container. If a process indicator is applied on the filter element, the user can also check whether the filter element has been subjected to a sterilization-type process.

In an advantageous exemplary embodiment according to the invention, the filter device is disposed or mounted on at least one first lateral wall of the tub-like first container part, especially from outside.

The installation or arrangement of the filter device on the cover or bottom of the sterilization container has proven to be disadvantageous in many respects. If the filtering device is on the cover, dust particles may be deposited on the filtering device during storage of the sterilization container. In addition, condensate dripping onto the cover-like component can enter the sterilization container during sterilization and complicate drying after sterilization. If the filter device is at the bottom, the filter device may be damaged when the sterilization container is handled, in particular by objects on a support, without this immediately becoming visible to the user. If, on the other hand, the filter device is mounted on a lateral wall, basically a small amount of dust can accumulate on it and the penetration of condensate is practically impossible. In addition, damage by objects on a bottom is virtually impossible. Mounting or arranging the filter device on a lateral wall of the sterilization container is therefore advantageous in many respects.

It is also advantageous if the first lateral wall of the tub-like first container part has a perforated filter device mounting section with lamellae and/or ribs pointing downwards/downwards and towards the inside of the container and/or the filter device has an externally provided perforated filter holder holding a filter element with lamellae and/or ribs pointing downwards/downwards and towards the outside of the container.

In other words, both a perforated filter device mounting section and a perforated filter holder, which allow sterile media exchange via the intermediate filter element, are provided in accordance with the invention. In contrast to the simple perforated plate type perforation known from the state of the art, the perforation in the present invention is formed by lamellae or ribs pointing downwards. These provide improved mechanical protection for the filter element, on the one hand, and allow condensate to drain off more effectively on the inside and/or outside of the container, on the other hand.

In an advantageous manner, the filter device mounting section and the filter holder have a gill-shaped perforated design, in particular with gills, preferably pressed out or in, in the form of narrow and/or elongate and/or channel-shaped and/or curved indentations.

In other words, the lamellae or ribs of the present invention have a gill-type design. Such a design provides optimum mechanical protection and enables a compact design, especially due to the gill-shaped arching or curvature. In addition, the gills can be easily manufactured by indentation forming in inward or outward direction, so that there are no disadvantages in this respect either, especially in comparison with perforated plate type perforations.

It is also advisable if gills and/or lamellae and/or ribs pointing towards the sterilization container outer side are provided on the filter holder and gills and/or lamellae and/or ribs pointing towards the container inner side are provided on the filter device mounting section and/or the gills and/or lamellae and/or ribs provided on the filter holder and the filter device mounting section are provided so as to be offset relative to each other in a lateral wall height direction.

If the externally provided filter holder is equipped with gills/lamellae/ribs pointing downwards and towards the outer side of the container, condensate can flow off outwards on the filter holder and thus not penetrate into the filter element. If the filter device mounting section is provided with gills/lamellae/ribs pointing downwards and towards the inside of the container, condensate can flow off inwards on the filter device mounting section and thus not penetrate into the filter element. The gills/lamellae/ribs are thus designed in such a way that draining condensate is directed away from the filter element both at the filter holder and at the filter device mounting section.

If the gills/lamellae/ribs of the filter device mounting section and of the filter holder are arranged to be offset in a sidewall height direction, the mechanical protection of the filter element is further improved. In particular, direct piercing from the outside into the sterilization container is then no longer possible.

In addition, the invention relates to a method for sterilizing, in particular a method for preparing a sterilization, of objects, in particular medical devices, in a sterilization container having a tub-like first container part and a cover-like second container part, in particular in a sterilization container as described above, comprising the steps: mounting a filter device, which is formed in particular by a filter holder and a filter element inserted therein, particularly from outside, on one of the container parts, in particular on a first lateral wall of the tub-like first container part; locking the filter device, in particular the filter holder, to the corresponding container part by means of a locking element; and closing the container parts with respect to one another via a sterilization container closure, in particular via a closing flap arranged on one of the container parts, and concomitant, in particular resultant, securing of the filter device to the container part on which the filter device is mounted, in particular to the first lateral wall of the tub-like first container part.

In an advantageous manner, the method according to the invention also comprises the following steps: Attaching a seal to the sterilization container closure; sterilizing objects which are to be sterilized and are located within the sterilization container; destroying the seal; and opening the sterilization container closure and concomitant, in particular resultant, releasing the filter device.

Furthermore, the invention relates to a sterilization container comprising a tub-like first container part, a cover-like second container part, a filter device which is arranged or mounted on at least one first lateral wall of the tub-like first container part from outside, wherein the first lateral wall has a filter device mounting section with gills and/or lamellae and/or ribs pointing downwards, in particular towards the sterilization container inner side, and the filter device has an externally provided filter holder which holds a filter element and has gills and/or lamellae and/or ribs pointing downwards, in particular to the sterilization container outer side, and wherein the gills and/or lamellae and/or ribs provided on the filter holder and the filter device mounting section are preferably arranged offset relative to one another in a sidewall height direction.

BRIEF DESCRIPTION OF THE DRAWING FIGURES

The invention is further explained below with the aid of Figures in which.

The Figures are merely schematic in nature and serve exclusively to help understanding the invention. Identical elements are marked with the same reference symbols.

DETAILED DESCRIPTION

Figure 1:
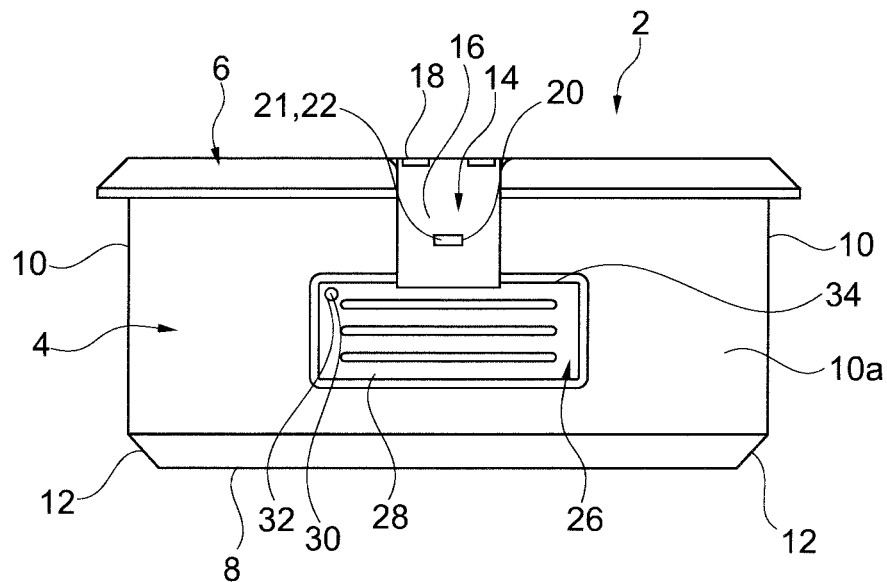
FIG. 1 is a side view of a sterilization container according to the present invention.

FIG. 1 shows a side view of a medical sterilization container 2. The latter consists of a tub-like first container part 4 and a cover-like second container part, in particular a cover 6. The container parts 4, 6 are preferably made of metal, in particular aluminum or stainless steel. However, both container parts 4 and 6 may also be made of plastic, in particular by injection molding. The tub-like first container part 4 consists of a bottom 8 and four lateral walls 10. In other words, the bottom 8 and the four lateral walls 10 together form the one-piece, one-material or integral tub-like first container part 4. In a transition area 12 from the lateral walls 10 to the bottom 8, the tub-like container part 4 is slanted, beveled or chamfered. The cover-like second container part 6 is also a one-piece, one-material or integral component separate from the tub-like container part 4. The cover-like second container part 6 is preferably pivotally mounted (not shown) on the tub-like first container part 4. However, according to the invention, it may also be completely removable from this.

FIG. 1 also shows a sterilization container closure 14 having a closing flap 16. The closing flap 16 is pivotally mounted on a hinge 18 on the cover type second container part 6 and is in a closed position in FIG. 1. In the closed position of the closing flap 16, the two container parts 4, 6 are closed to one another. The closing flap 16 has a receiving recess 20 in which a latching element 21 is received. A seal 22 can be inserted through the latching element 21. In its closed position, the closing flap 16 is thus engaged in the latching element 21 and a seal 22 mounted to the latching element 21 secures the sterilization container closure 14.

On the first lateral wall 10*a* completely visible in FIG. 1 a filter/filter device 26 is disposed or mounted from outside/from a sterilization container outer side 24. The filter device 26 consists of a filter holder 28 and a filter element 30. The filter holder 28 has a window 32 through which a user can see the inserted filter element 30. In case a process indicator is mounted to the filter element 30, a user can check whether the filter element 30 has been sterilized in the desired manner or not. The closing flap 16 overlaps the filter device 26 in FIG. 1 in part at an upper edge area 34 of the filter device 26. According to the invention, it is also conceivable that the closing flap 16 overlaps either only the filter element 30 or only the filter holder 28. In FIG. 1, horizontally aligned and thus parallel, elongated and narrow longitudinal recesses are indicated on the filter device 26 and in particular on the filter holder 28, which, as will become clear in the following description in relation to FIG. 2, are intended to represent a gill-shaped perforation of the filter holder 28.

Figure 2:
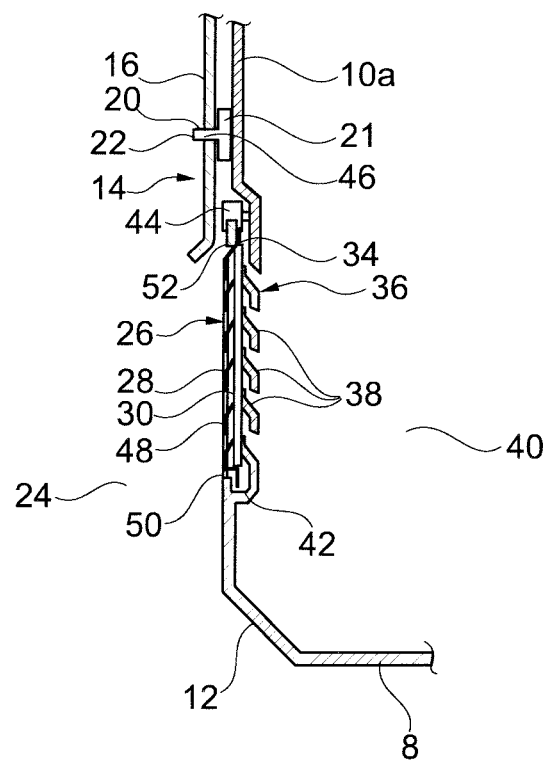
FIG. 2 is a cross-sectional view illustrating the interaction, according to the invention, between a filter device, a closing flap and a lateral wall of the sterilization container of the present invention.

FIG. 2 illustrates the interaction, according to the invention, between the filter/filter device 26, the closing flap 16 and the first lateral wall 10*a* in a sectional view.

The first lateral wall 10*a* has a filter device mounting section 36. The filter device mounting section 36 has a gill-shaped perforated design and comprises a plurality of gills 38. The gills 38 are generally narrow, elongated or deepened in trough shape, have an arched/curved design and are manufactured by pressing in outward or inward direction. The gills 38 each point downwards or to the bottom 8 of the sterilization container 2 and to the sterilization container inner side 40. The gills 38 have a domed/curved arched shape in the manner of a half-parabola open to the bottom, with a low initial slope and an approximately proportionally increasing slope. A groove-shaped indentation 42 is provided at a lower section of the filter device mounting section 36. The filter device mounting section 36 is designed so as to be slightly offset to the inside with respect to the lateral wall 10*a*, on which the filter device mounting section 36 is provided, or to the sterilization container inside 40.

Towards the top, the filter device mounting section 36 is limited by a locking element 44 mounted to the lateral wall 10*a*. The locking element 44 can basically be mounted in spring-loaded manner as a separate component in the lateral wall 10*a*. However, the locking element 44 can also be firmly connected to the lateral wall 10*a*. Furthermore, it is conceivable that the locking element 44 is formed in one piece/in one-material fashion/integrally with the lateral wall 10*a*.

Above the filter device mounting section 36, the first lateral wall 10*a* has the latching element 21, which in FIG. 2 is a component which is separate from the lateral wall 10*a* but firmly connected to it. The latching element 21 has a latching projection 46 which protrudes or projects towards a sterilization container outer side 24.

The filter device 26 consists of the filter holder 28 and the filter element 30 held or mounted to it. The filter holder 28 has gills 48 which, just like the gills 38 of the filter device mounting section 36, are narrow, elongated or deepened in trough shape, have an arched/curved design and are manufactured by pressing in outward or inward direction. The gills 48 each point downwards or to the bottom 8 of the sterilization container 2 and to the sterilization container outer side 24. The gills 48 also have a domed/curved arched shape in the manner of a half-parabola open to the bottom, with a low initial slope and an approximately proportionally increasing slope towards the bottom.

The gills 48 can have a spring action/act as spring elements which press the filter element 30 against the filter device mounting section 36. The gills 48 overlap preferably in height direction/vertical direction and are only open towards the bottom. Also the gills 38 preferably overlap in height direction and are only open towards the bottom. The filter element 30 is thus covered/protected in the side direction.

When installing the filter device 26, a lower edge area 50 of the filter device 26 is inserted/attached/received in the groove-shaped indentation 42, and the filter device 26 is pressed manually against the first lateral wall 10*a*. The locking element 44 then locks the filter device 26, in particular the filter holder 28, to the first lateral wall 10*a*. Finally, the closing flap 16 is folded downwards and engages in the latching element 21, whereby the tub-like first container part 4 and the cover-like second container part 6 are locked together. A covering section 52 of the closing flap 16 overlaps or covers the upper edge area 34 of the filter device 26 and, preferably when the two container parts 4, 6 are locked to each other, can press it against the filter device mounting section 36 and the first lateral wall 10*a*, respectively.

In the closed position of the closing flap 16, the latching element 21 or in particular the latching projection 46 of the latching element 21 projects outwards with respect to the closing flap 16. The latching element 21 has a not shown recess or the like through which the seal 22 can be put. If the sterilization container 2 is additionally sealed with the seal 22 in the closed position of the closing flap 16, the sterilization container 2 can only be reopened by destroying the seal 22. Only after the seal 22 has been destroyed and the sterilization container has been opened again, the filter device 26 can be detached from the filter device mounting section 36 or the first lateral wall 10*a*. In other words, the filter can only be removed when the seal 22 has been destroyed after sterilization.

By aligning the gills 38 of the filter device mounting section 36 downwards and towards the sterilization container inner side 40, condensate water coming from above is diverted away from the filter element 30 when dripping off. By aligning the gills 48 of the filter holder 28 downwards and towards the sterilization container's outer side 24, condensate coming from above is also diverted away from the filter element 30 when dripping off.

Figure 3:
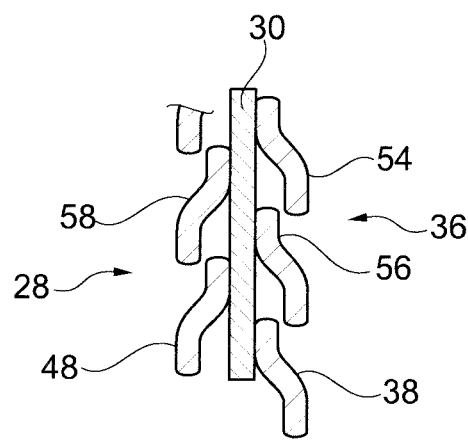
FIG. 3 is a detailed view of a preferred embodiment of the filter device and a filter device mounting section provided on the lateral wall.

FIG. 3 shows a detailed view of a preferred embodiment of the filter device 26 and the filter device mounting section 36 provided on the lateral wall 10*a*. The filter device 26 again consists of the filter holder 28 and the filter element 30. In FIG. 3, the gills 38 of the filter device mounting section 36 are designed in overlapping form. In other words, a gill end section 54 of an upper gill 38 overlaps a gill starting section 56 of a lower gill 38 in each case. The same applies to the gills 48 of the filter holder 28. Here too, a gill end section 54 of an upper gill 48 overlaps a gill starting section 56 of a lower gill 48. This serves in particular to protect the filter element 30. In order to further improve the protection of the filter element 30, the gills 38 and 48 are also designed or arranged so as to be offset relative to one another. In other words, a gill starting section 56 and a gill end section 54 of the gills 38 each coincide with a gill center section 58 of the gills 48, as seen in a sidewall height direction.

Figure 4:
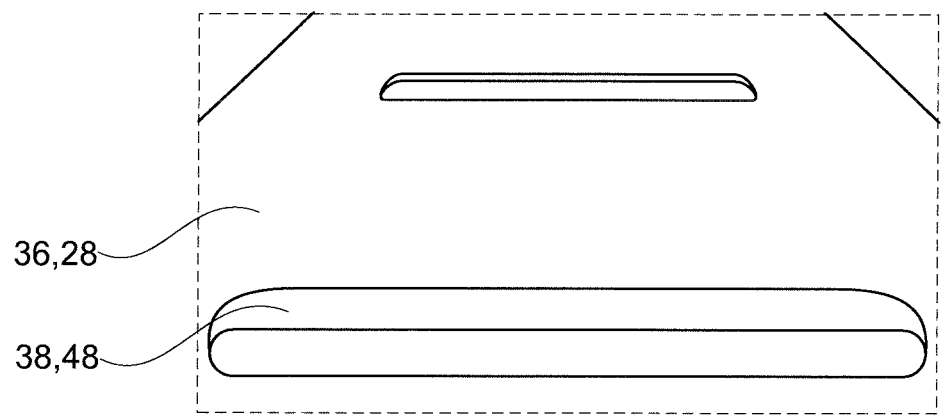
FIG. 4 is a perspective view of gills pressed in/out, as they may be provided on the filter device mounting section or a filter holder of the filter device.

Finally, FIG. 4 shows a perspective view of gills 38, 48 pressed in/out as they may be formed or provided on the filter holder 28 of the filter device 26 or the filter device mounting section 36. In particular, the narrow, elongated, channel-shaped deepened and arched/curved design of the gills 38, 48 becomes even more visible here.

The invention claimed is:

1. A sterilization container comprising:
a first container part,
a second container part,
a filter device which is disposed or mounted on at least one of the first container part and the second container part;
and a sterilization container closure which comprises at least one closing flap which is configured to be disposed on one of the first and second container parts between a closed position and an open position for the purpose of closing the first and second container parts, the at least one closing flap being pivotally mounted, wherein,
when in the closed position, said at least one closing flap locks and/or fastens and/or secures the filter device to said at least one of the first container part and the second container part.

2. The sterilization container according to claim 1, wherein the filter device comprises an externally provided filter holder and a filter element held on the filter holder, and the filter holder has a window for a user to check a state of the filter element from a sterilization container outer side.

3. The sterilization container according to claim 2, wherein the filter device is disposed or mounted on at least one first lateral wall of the first container part.

4. The sterilization container according to claim 3, wherein the at least one first lateral wall of the first container part has a perforated filter device mounting section with downwardly pointing lamellae and/or ribs and/or the filter device has an externally provided perforated filter holder holding a filter element and having downwardly pointing lamellae and/or ribs.

5. The sterilization container according to claim 4, wherein the filter device mounting section and the filter holder have a gill-shaped perforated design comprising narrow and/or elongate and/or channel-shaped and/or curved indentations.

6. The sterilization container according to claim 4, wherein gills and/or lamellae and/or ribs pointing towards the sterilization container outer side are provided on the filter holder and gills and/or lamellae and/or ribs pointing towards a container inner side are provided on the filter device mounting section and/or the gills and/or lamellas and/or ribs provided on the filter holder and the filter device mounting section are provided so as to be offset relative to each other in a lateral wall height direction.

7. The sterilization container according to claim 1, wherein said at least one of the first container part and the second container part, on which the filter device is disposed or mounted, has a seating or recess and a locking element.

8. The sterilization container according to claim 7, wherein the filter device, in the open position of the at least one closing flap, is configured to be inserted and/or mounted in the seating or recess from a sterilization container outer side, and configured to be fixed and/or locked via the locking element to said at least one of the first container part and the second container part.

9. The sterilization container according to claim 1, wherein the sterilization container closure comprises a latching element on said at least one of the first container part and the second container part.

10. The sterilization container according to claim 9, wherein the closing flap is engaged in the latching element in the closed position, thereby locking the first and second container parts to one another and covering the filter device at least in sections.

11. A sterilization container comprising:
a first container part,
a second container part,
a filter device which is disposed or mounted on at least one of the first container part and the second container part;
and a sterilization container closure which comprises at least one closing flap which is configured to be disposed on one of the first and second container parts between a closed position and an open position for the purpose of closing the first and second container parts, wherein,
when in the closed position, said at least one closing flap locks and/or fastens and/or secures the filter device to said at least one of the first container part and the second container part, wherein
said at least one of the first container part and the second container part, on which the filter device is disposed or mounted, has a seating or recess and a locking element, and
the sterilization container closure comprises a latching element on said at least one of the first container part and the second container part, wherein
the filter device, in the open position of the at least one closing flap is configured to be inserted and/or mounted in the seating or recess from a sterilization container outer side, and configured to be fixed and/or locked via the locking element to said at least one of the first container part and the second container part, and wherein
the closing flap is engaged in the latching element in the closed position, thereby locking the two container parts to one another and covering the filter device at least in sections.

12. The sterilization container according to claim 11, wherein the latching element, in the closed position of the at least one closing flap is received in a receiving recess provided on the at least one closing flap, and a seal for sealing the sterilization container and for securing the sterilization container closure in the closed position of the at least one closing flap is configured to be passed through the latching element.

13. A sterilization container comprising:
a first container part,
a second container part,
a filter device which is arranged or mounted on at least one first lateral wall of the first container part from outside,
wherein
the at least one first lateral wall has a filter device mounting section with gills and/or lamellae and/or ribs pointing downwards, and the filter device has an externally provided filter holder which holds a filter element and has gills and/or lamellae and/or ribs pointing downwards.

14. A method for sterilizing objects in a sterilization container, the sterilization container having a first container part and a second container part, comprising the steps of:
mounting a filter device on one of the first container part and the second container part;
locking the filter device to said one of the first container part and the second container part by a locking element; and
closing the first and second container parts with respect to one another via a closing flap, which is pivotally mounted, and a concomitant, securing of the filter device to said one of the first container part and the second container part.

15. The method for sterilizing objects in a sterilization container according to claim 14, further comprising the steps of:
inserting and/or mounting the filter device in a seating or recess from a sterilization container outer side; and
engaging the closing flap in a latching element, thereby locking the first and second container parts to one another and covering the filter device at least in sections.

\* \* \* \* \*